United States Patent [19]

Douklias

[11] Patent Number: 4,501,492
[45] Date of Patent: Feb. 26, 1985

[54] METHOD FOR TESTING SPECIMENS

[75] Inventor: Nikolaos Douklias, Kirchheim, Fed. Rep. of Germany

[73] Assignee: Siemens Aktiengesellschaft, Berlin & Munich, Fed. Rep. of Germany

[21] Appl. No.: 392,587

[22] Filed: Jun. 28, 1982

[30] Foreign Application Priority Data

Jul. 3, 1981 [DE] Fed. Rep. of Germany ....... 3126356

[51] Int. Cl.³ .................... G01N 21/84; G01N 21/89
[52] U.S. Cl. .................................. 356/73.1; 65/29; 65/160
[58] Field of Search ............... 356/73.1, 71; 65/29, 65/160

[56] References Cited

U.S. PATENT DOCUMENTS 3,539,260 11/1970 Burch ................................. 356/71
3,658,420 4/1972 Axelrod .............................. 356/71
3,743,423 7/1973 Heinz et al. ......................... 356/71

OTHER PUBLICATIONS

Kitayama et al., "Determination of Mode Power Distribution in a Parabolic-Index Optical Fibers: Theory and Application", IEEE J. of Quan. Electronics, vol. QE-15, No. 10, Oct. 1979, 1161-1165.
H. M. Presby et al., "Optical Fiber Preform Diagnostics", Applied Optics, vol. 18, No. 1, Jan. 1, 1979, pp. 23-30.

Primary Examiner—Vincent P. McGraw
Attorney, Agent, or Firm—Hill, Van Santen, Steadman & Simpson

[57] ABSTRACT

A method and device for testing specimens, such as optical fibers or preforms from which optical fibers are produced, to discover defects in the specimen includes creating a spatial frequency spectrum of the specimen, filtering the spectrum by projecting it onto a spatial frequency filter and evaluating the portion or component of the spectrum passing through the filter.

14 Claims, 1 Drawing Figure

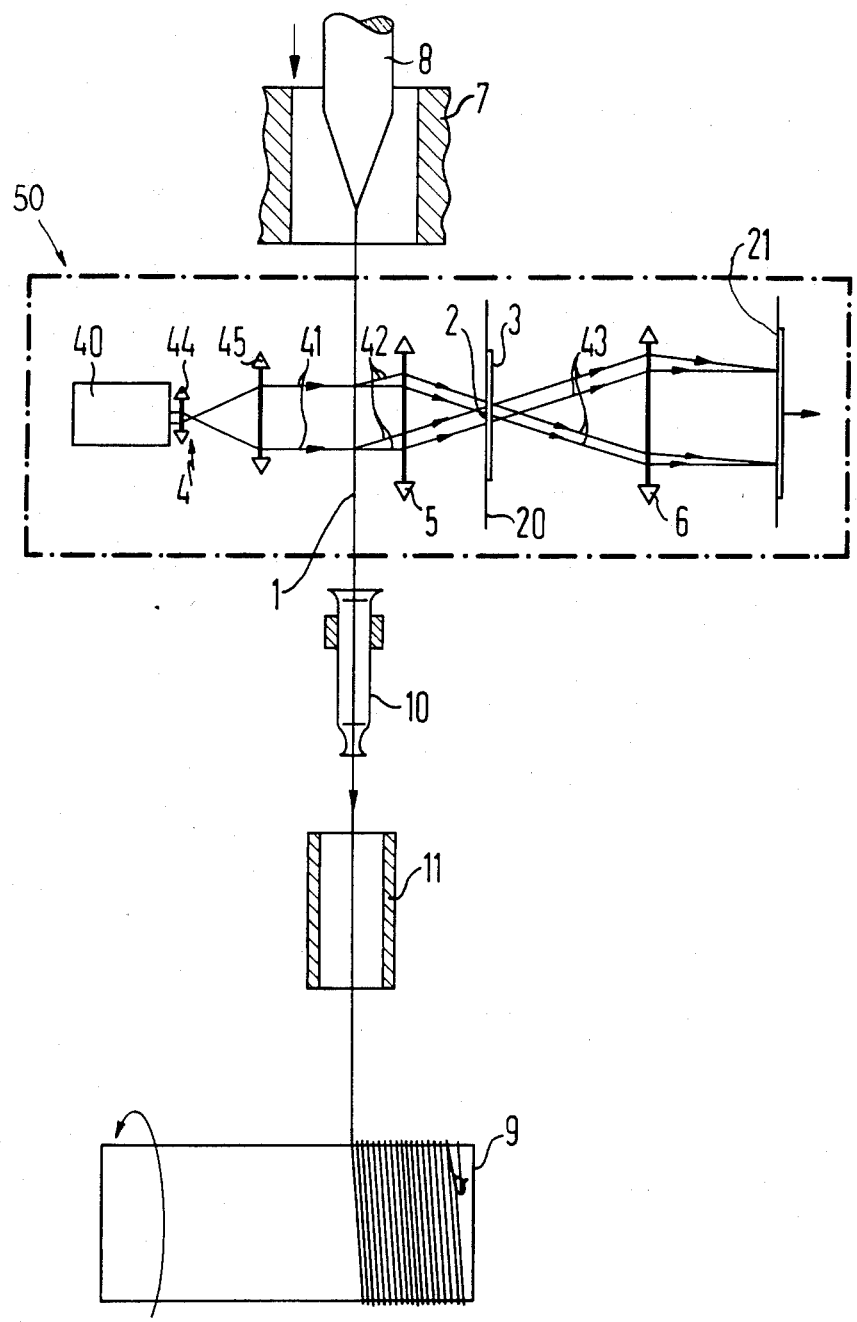

METHOD FOR TESTING SPECIMENS

BACKGROUND OF THE INVENTION

The present invention is directed to a method for testing specimens such as optical fibers or preforms which are used to manufacture optical fibers.

Optical fibers for optical message transmission must exhibit good optical properties. These properties include, for example, low attenuation, large numerical aperture and low pulse spread as well as a sufficiently high tensile strength. In order to protect the fiber surface against mechanical and chemical damage, the optical fibers are usually coated during the drawing process by applying a synthetic coating thereto. Frequently, however, even coated fibers will exhibit a low strength, for example, because oven particles or foreign particles will damage the fiber surface while the fiber is still in the oven chamber and because other impurities were already present in the preform from which the fiber was drawn. The strength of the fiber will depend on the frequency and the size of these defects which will be statistically distributed over the entire fiber length.

At present, the strength of the fiber is tested in the following manner. Long fibers, which are usually more than one kilometer long are generally divided into fiber pieces which are approximately 20 meters long and these fiber pieces are loaded in tension in a testing installation until they fracture. From the statistical evaluation of the tensile forces utilized to fracture the individual specimens, a prediction concerning the achievable strength and the strength to be expected in other fibers can be derived according to the so-called Weibull method.

Frequently, the fibers are subjected to a so-called screen test after coating. Thus, the fiber is conducted over rollers and is loaded with a minimum tensile force over its entire length which minimum tensile force would not break the fiber. The mechanical contact of the fiber with the rollers under these tensile stresses can lead to damage to the synthetic coating and to the fiber surface and thus leads to a reduction in the fiber strength.

In order to test preforms such as applied fiber rods from which optical fibers are to be drawn, the preforms are examined by rather imprecise methods. Examples of these methods are disclosed in an article by H. M. Presby et al, "Optical Fiber Preform Diagnostics", *Applied Optics,* Vol. 18, No. 1, Jan. 1, 1979, pp. 23-30.

SUMMARY OF THE INVENTION

The present invention is directed to a method of non-destructively and reliably testing optical specimens as to the rated properties, which optical specimens are understood to include both optical fibers and optical preforms from which optical fibers are manufactured. In particular, the optical fibers are to be able to be tested non-destructively and reliably as to their tensile strength.

The object of the present invention is accomplished by producing or creating a spatial frequency spectrum of the specimen or at least a part thereof; filtering the spectrum by projecting it onto a spatial frequency filter; and evaluating the portion or component of the spectrum passing through said filter.

In conjunction with the optical fibers in the solution, the invention proceeds from the perception that the strength of the fiber depends on the frequency and the size of the defects which are statistically distributed over the entire fiber length and that knowledge concerning the location and size of the defects will suffice in order to gain a statement or prediction concerning the fiber strength without sample pieces needing to be cut according to the previously known methods. The location of the defect in the preform from which an optical fiber is drawn will lead to a similar statement or prediction as to the expected tensile strength of the fiber.

In conjunction with optical fibers, the specific solution of the present invention exhibits an advantage that all defects are identified in terms of their position, size and nature so that a reliable statement or prediction concerning the expected tensile strength of the fiber can be provided. Therefore, the method functions non-destructively.

In contrast to the method of the present invention, previously known methods in which the fiber was cut and destroyed would not detect all the defects of the fiber and only detected those defects which led to the lowest tensile strength in the specimen. Thus, defects, which reduced the tensile strength of the fiber but did not lead to a minimum tensile strength but rather to a higher one, were not identified in the prior art methods.

The proposed method, however, can be employed not only for testing optical fibers or preforms but can be generally employed for the non-destructive testing of physical specimens as to their rated or specific properties. For example, physical objects can be inspected in terms of their shape or size as to their coincidence with the prescribed rated shape or size.

For example, one can proceed in a method in which the step of filtering the created spectrum by projecting it onto a spatial frequency filter includes providing a spatial frequency filter which exhibits the spatial frequency specimen of an object with the desired properties, which object is defect-free or exhibits a particularly prescribed or rated property.

The spatial frequency filter can, for example, be photographically reproduced. However, producing the filter by the assistance of the computer and plotter is often more advantageous because greater differences of the intensity which can lead to problems in photographic exposures can be balanced out. With particular objects to be achieved and with only certain defects being selected, the method can be utilized with a spatial frequency spectrum filter which consists of a simple structure in which not all but rather only certain relatively strong appearing diffraction maximums of the spatial frequency spectrum are at least partially removed or blocked out.

In particular, this method can be applied with transparent fibers, particularly glass fibers for optical communication technology or the rod-like preforms from which these fibers are produced. Thus, the diffraction maximums of the spatial frequency spectrum which lie on a line proceeding or extending at right angles relative to the axis of the fiber or the rod are at least partially blocked out with an elongated opaque strip or a similar elongated structure because the shape of these objects and the ordered defects appear in the form of elongated fluting.

An evaluation is expediently carried out on the light which passes through the filter. This evaluation can be made by reconstructing the image contained in encoded form in the light which is passed through the spatial filter and then evaluating the reconstructed image.

It is expedient to visually evaluate the light which has passed through the spatial frequency filter or the reconstructed image by receiving the light or image on a television camera or by receiving the light or image with a detector array and plotting the output of the detector array with a plotter and computer. However, the evaluation can also be carried out by sampling and evaluating the intensity of the light which passes through the spatial frequency filter.

It should be noted that the present method is advantageously utilized for testing moving objects. Thus, it is particularly useful in testing fiber-shaped or rod-shaped objects as they are passing through a drawing apparatus. In order to carry out the method, the invention includes a device having means for creating a coherent light beam and projecting it into a spectrum, transformation lens which is disposed on the beam axis for receiving the light from the specimen and having a focal plane, and a spatial frequency filter located on the focal plane. Given fibers which are drawn in a drawing process, for example, optical fibers, but also in the case of wires, one expediently proceeds in such a manner that the device is located so that the freshly drawn fiber is already drawn through the light beam during the drawing process and the spatial frequency spectrum produced by the illuminated section of the fiber is continuously evaluated. A particular advantage of the inventive method is that translational variance, which, for example, effects that movement of the fiber to be tested perpendicularly to its axis, does not influence the spatial frequency spectrum.

BRIEF DESCRIPTION OF THE DRAWINGS

The FIGURE is a schematic illustration of a device in accordance with the present invention which enables continuous inspection in accordance with the present invention.

DESCRIPTION OF THE PREFERRED EMBODIMENTS

The principles of the present invention are particularly useful in a device generally indicated at 50 and schematically illustrated in a fiber drawing device in which a glass fiber is drawn from an optical rod and the freshly drawn fiber is continuously inspected by the testing device 50 of the present invention.

The fiber drawing device illustrated in the FIGURE comprises an annular drawing furnace 7 in whose opening the lower end of a rigid fiber rod 8 is disposed. The drawing furnace 7 causes the lower end of the rigid fiber rod to melt and an optical fiber 1 is drawn from the melted end of the rod 8 from the melting zone. This occurs by means of a drawing drum 9 onto which the fiber 1 is wound and via which the drawing rate is also determined.

Before the fiber 1 is wound onto the drawing drum 9, it can also be passed through a coating device 10 which will apply a coating comprising a synthetic layer. After having the synthetic layer applied to the fiber, the fiber passes through a drying kiln 11 in which the soft synthetic layer is hardened.

The device 50 for testing the fiber 1 comprises a light source 4, which generates a coherent parallel light beam 41 which illuminates the fiber 1 at right angles relative to its axis. The light source 4 consists of a laser 40 and a lens system or telesystem, which is constructed of two positive lenses 44 and 45, which lens system serves as a beam spreading optics. In the present case, a cylindrical lens can also be utilized as the positive lens because the beam spread is only required in the longitudinal direction of the fiber 1.

A transformation lens 5 is disposed in a beam path 42 of the light which path 42 created by the light that is passed through the fiber 1. This transformation lens has a focal plane 20 which is on a side opposite from the light source. The transformation lens will produce a spatial frequency spectrum belonging to the illuminated section of the fiber 1 in this focal plane 20. The transformation lens 5 consists of a spherical positive lens, preferably an objective. However, it can also be a cylindrical positive lens.

A spatial frequency filter 3 is positioned in the focal plane 20. The spatial frequency filter 3 can, for example, consist of a photographic plate or of a film on which the spatial frequency spectrum 2 has been recorded. The spatial frequency filter 3 can be the spatial frequency spectrum of a defect-free fiber piece and thus the spectrum of a specimen which exhibits the rated or the desired properties.

A spatial frequency filter can be produced, for example, by using the same device 50. This is accomplished by placing a defect-free fiber piece in the beam path 41 in the position which is illustrated by the fiber 1. A photographic plate is then placed in the focal plane 20 and exposed with a spatial frequency spectrum which is produced by projecting the beam 41 through the defect-free fiber piece. The developed photographic plate then forms a spatial frequency filter 3 which, however, then does not contain the positive of the spatial frequency spectrum with the rated or special properties but rather is a negative with a black/white information. This, however, has the advantage that the spatial frequency filter 3, when it has been placed in coincidence with a spatial frequency spectrum, produced by a fiber 1, only allows light to pass which transmits information concerning defects of the fiber or general deviations from the rated or special properties of the fiber whereas all remaining light will be blanked out. In this manner alone, information concerning the position, size and nature of the defects can be identified and evaluated.

If, for example, the fiber 1 exhibits no faults or defects, then the same spatial frequency spectrum will occur as was produced by the defect-free fiber piece which was used to produce the spatial frequency filter 3. When this spatial frequency spectrum is superimposed with the spatial frequency spectrum of the spatial frequency filter 3, which is illustrated in the negative, in such a manner that the intensity maximums and minimums of the spatial frequency spectrum coincide with the intensity maximums and minimums of the photographic plate, then because of the identity of the two spatial frequency spectra, no light can pass through the photographic plate. When in contrast thereto, the fiber 1 contains defects, light will be diffracted or scattered at the locations of the defects which means that light will now be at light transmissive locations on the photographic plate and pass through the filter.

The light, which is passed through the spatial frequency filter 3, is transformed back by an inverse transformation lens 6 which likewise consists of a positive lens. A real image only of the faults or defects contained in the illuminated fiber piece of the fiber 1 occurs in an image plane 21 which is allocated to the focal plane 20 in this back transformation. This fault or defect could be evaluated with various methods. For example, it may be evaluated visually by use of a television camera or by a light-sensitive detector array and a computer or a plotter.

The continuous evaluation of the reproduced image provides information, for exanple, concerning the position, nature and size of the defects and also, for example, whether it is a matter of particles, fluting or fluctuations in the index of refraction. However, fluctuations in the diameter of the fiber can also be detected so that the method is also suitable as a diameter-resting device for fibers.

Given optical fibers but also given other transparent fibers, for example, plastic fibers, a peculiarity occurs insofar as fluting in the fiber surface frequently occurs as a defect. This fluting moreover usually proceeds or extends in a longitudinal direction of the fiber. Such flutings are longitudinal structures and thus are configurationally similar to the fibers themselves in a certain manner.

These flutings are phase objects, which essentially change only the phase and thus the direction of the penetrating light. Because of this configurational similarity to the fiber, the fluting, which extends approximately in the longitudinal direction of the fiber, changes the directional light in a manner similar to that of a phase object fiber itself. That means that the diffraction maximums produced by the fluting in the focal plane essentially lies on a line in the focal plane which is perpendicular to the fiber axis.

The diffraction maximums, which are produced by other fiber defects and which do not exhibit an ordering corresponding to the fluting, are aligned in the longitudinal direction of the fiber. For example, dirt particles or other defects, which are light-absorbent and thus form amplitude objects or statistical fluctuations of the index of refraction, in contrast thereto, also occur outside of the line and next to the diffraction maximums produced by the fiber and by the longitudinal flutings.

In comparison to the diffraction maximums produced by other fiber defects, particularly by the amplitude objects, the diffraction maximums lying on the line and produced by the fiber and the longitudinal flutings appear with a relatively high contrast.

The intensity or brightness difference, which is both within each diffraction maximum as well as between the diffraction maximum, can be so great in fibers particularly even in the case of defect-free fibers that an over-exposure or an under-exposure of the photographic film or of the photographic plate occurs in a photographic picture of the spatial frequency spectrum. As a result, photographic production of the spatial frequency spectrums can lead to some difficulties.

These difficulties can be eliminated in that the spatial frequency spectrum of the filter is not photographically produced, but rather is synthetically produced with the assistance of a computer and of a plotter. This method can be employed not only in the case of fibers but can also be advantageously employed everywhere a high intensity or brightness difference in the photographic exposure of the spatial frequency spectrum leads to difficulties.

The peculiarities appearing in given fibers, namely the longitudinal fluting frequently occurring as a fiber defect, makes a further, particularly simple but effective method possible for testing such fibers. Since, as already mentioned, the diffraction maximums produced by the fiber itself and by the longitudinal flutings on the same line are relatively strong in comparison to the maximums produced by the remaining fiber defects, the fiber and these longitudinal flutings dominate the appearance in the reconstructed image when no spatial frequency filtration is carried out. Other faults, particularly amplitude objects, now either hardly appear at all or do not appear.

It has now been discovered that fiber defects can be made more clearly visible when only the diffraction maximums lying on the said line in the focal plane and thus produced by the fiber itself and the longitudinal fluting are at least partially blanked out.

However, an opaque structure, whose shape is similar to that of the fiber itself, is disposed in the light beam path in such a manner that all diffraction maximums lying on said line in the focal plane are at least partially blanked out. A wire or an opaque strip will suffice for this purpose.

The contrast of the reconstructed image can be continuously varied over the degree to which these diffraction maximums are blocked out. Amplitude objects appear all the more clearly, the more the strong diffraction maximums lying on said line are blocked out or removed. However, phase objects will appear all the more clearly when fewer of these strong maxminums are blocked out. The degree to which the strong maximums are blocked out can be adjusted over the diameter or the width of the wire or respectively the strip.

The method which was just described can always be advantageously employed when a certain defect occurs in a specimen to be tested with particular frequency, said defect consists of a phase object, or all of these phase objects are similar in shape and have essentially the same orientation. These ordered phase objects can interact in the production of the spatial frequency spectrum in such manner that they lead to relatively strong diffraction maximums in the spatial frequency spectrum when the order of the phase objects is reflected. Moreover, the conditions are particularly favorable when the specimen to be tested is itself a phase object to which each of the said ordered phase objects is similar in terms of shape and is essentially oriented in the same manner as the specimen itself. The prerequisite for the applicability of this method, however, is that diffraction maximums of other defects, particularly of amplitude objects, are present beyond the diffraction maximums produced by the ordered phase objects and, under certain conditions, by the specimen. Given this precondition, the spatial frequency filtration can then be frequently undertaken with a structure which is similar in shape to the specimen or to one of the ordered phase objects.

As has already been previously pointed out, the rigid fiber rod 8 can also be employed for testing the curve of the index of refraction and the fiber strength, whereby it would then only be necessary to illuminate this rod with a coherent light beam and to generate a spatial frequency spectrum from it. Thus, each of the three possibilities of spatial frequency filtration described above can be employed, i.e., the filtration can be undertaken with a photographically produced spatial frequency filter, or with an elongated strip or a similar structure proceeding perpendicularly relative to the axis of the rod. As in the case of the fiber, one will select the method best suited for the particular case.

Given the device illustrated in the FIGURE, a displacement of the specimen to be tested, i.e., of the fiber 1, has no negative effect because the method is translationally invariant.

In conclusion, it should be expressly pointed out that, given the method for inspecting glass fibers described hereinabove, defects can be located either in a preform for drawing of the fiber or directly during fiber-drawing and before the coating of the fibers and the size of the defect can be estimated. By so doing, it is possible to non-destructively inspect optical fibers for optical communication transmission, particularly as to their resistance to tearing. In addition, the inspection will determine fluctuations in the index of refraction and these conclusions can be made concerning the transmission properties of the fibers. Fluctuations in thickness can also be measured by the method.

It should also be expressly emphasized that the method is not restricted to the inspection of glass fibers but that it can be generally employed as a method for the non-destructive testing of other specimens.

Although various minor modifications may be suggested by those versed in the art, it should be understood that I wish to embody within the scope of the patent granted hereon, all such modifications as reasonably and properly come within the scope of my contribution to the art.

I claim:

1. A method for non-destructive testing of fiber optical waveguides as to their tensile properties, said method comprising the steps of providing a specimen selected from a fiber optical waveguide and a preform from which a fiber optical waveguide is drawn; creating a spatial frequency spectrum of the specimen; filtering the spectrum to remove selected relatively stronger-appearing diffraction maximums of the spatial frequency spectrum by projecting the spectrum of the specimens onto a spatial frequency filter; and evaluating the component of the spectrum passing through the filter.

2. A method according to claim 1, wherein the step of filtering the spectrum by projecting it onto a spatial frequency filter includes providing a spatial frequency filter which exhibits a spatial frequency spectrum of a specimen with the desired tensile properties.

3. A method according to claim 2, wherein the step of providing the spatial frequency filter includes photographically producing the spatial frequency filter.

4. A method according to claim 2, wherein the step of providing the spatial frequency filter includes synthetically producing the filter with the assistance of a computer and plotter.

5. A method according to claim 1, wherein the step of filtering the spectrum by projecting it onto a spatial frequency filter includes providing a filter with a spatial frequency spectrum which consists of a simple structure with selected relatively strong appearing diffraction maximums of the spectrum being at least partially blocked out.

6. A method according to claim 5, wherein providing a filter includes providing opaque strips and elongated structures to partially block out diffraction maximums of the spatial frequency spectrum which extend on a line proceeding at right angles relative to the axis of the specimen.

7. A method according to claim 1, wherein the step of evaluating the component of the spectrum passing through said filter includes evaluating the light that passes through said filter.

8. A method according to claim 7, wherein the light which passes through the spatial frequency filter contains an image in encoded form and said step of evaluating includes reconstructing said image for evaluation.

9. In a method according to claim 7, wherein said step of evaluating the light passing through said filter includes receiving said light television camera.

10. A method according to claim 7, wherein said step of evaluating the light passing through said filter includes receiving the light with a detector array and utilizing a plotter to plot the output of said array.

11. A method according to claim 7, wherein the step of evaluating the light passing through said filter includes sampling and evaluating the intensity of the light passing through said filter.

12. A method according to claim 1 which is utilized for inspecting a fiber being drawn during the drawing process, said method including the step of creating the spatial frequency spectrum by projecting a light beam on a freshly drawn fiber as it is being drawn from a preform.

13. A device for non-destructive testing of a fiber optical waveguide as to its tensile properties by a method of drawing a fiber optical waveguide from a preform, creating a spatial frequency spectrum of a portion of the waveguide, filtering the spectrum by projecting it onto a spatial frequency filter and evaluating a component of the spectrum passing through said filter, said device comprising means for producing a beam of coherent light and projecting it onto a fiber optical waveguide being drawn from a preform; a transformation lens being disposed on a beam axis of said beam of light in a position to receive the light passing through said waveguide, said transformation lens having a focal plane; a spatial frequency filter being disposed in said focal plane and means for evaluating components of said frequency spectrum passing through said filter.

14. A method for non-destructive testing of a fiber optical waveguide as to its tensile properties, said method comprising the steps of drawing an optical fiber waveguide from a preform, creating a spatial frequency spectrum of the waveguide; filtering the spectrum by providing a filter with a spatial frequency spectrum which consists of a simple structure that will partially block out selected relatively strong appearing diffraction maximums of the spectrum and by projecting the spectrum of the waveguide onto said spatial frequency filter and then evaluating the components of the spectrum passing through the filter.

* * * * *